United States Patent
Bae et al.

(10) Patent No.: US 11,345,671 B2
(45) Date of Patent: May 31, 2022

(54) PHENYLSULFONYL OXAZOLE DERIVATIVE AND USE THEREOF

(71) Applicants: KYUNGPOOK NATIONAL UNIVERSITY INDUSTRY-ACADEMIC COOPERATION FOUNDATION, Daegu (KR); INDUSTRY-ACADEMIC COOPERATION FOUNDATION, YONSEI UNIVERSITY, Seoul (KR); GWANGJU INSTITUTE OF SCIENCE AND TECHNOLOGY, Gwangju (KR); SEOUL NATIONAL UNIVERSITY R&DB FOUNDATION, Seoul (KR)

(72) Inventors: Jae Sung Bae, Daegu (KR); Hee Kyung Jin, Daegu (KR); Myung Shik Lee, Seoul (KR); Hye Jin Lim, Seoul (KR); Jin Hee Ahn, Gwangju (KR); Haushabhau Shivaji Pagire, Gwangju (KR); Min Jae Lee, Seoul (KR)

(73) Assignees: KYUNGPOOK NATIONAL UNIVERSITY INDUSTRY-ACADEMIC COOPERATION FOUNDATION, Daegu (KR); INDUSTRY-ACADEMIC COOPERATION FOUNDATION, YONSEI UNIVERSITY, Seoul (KR); GWANGJU INSTITUTE OF SCIENCE AND TECHNOLOGY, Gwangjui (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 16/961,348

(22) PCT Filed: Jan. 10, 2019

(86) PCT No.: PCT/KR2019/000373
§ 371 (c)(1),
(2) Date: Jul. 10, 2020

(87) PCT Pub. No.: WO2019/139365
PCT Pub. Date: Jul. 18, 2019

(65) Prior Publication Data
US 2021/0070718 A1    Mar. 11, 2021

(30) Foreign Application Priority Data
Jan. 10, 2018   (KR) ........................ 10-2018-0003586

(51) Int. Cl.
*C07D 263/46*    (2006.01)
(52) U.S. Cl.
CPC ................................. *C07D 263/46* (2013.01)
(58) Field of Classification Search
CPC .................................................. C07D 563/46
See application file for complete search history.

(56) References Cited

FOREIGN PATENT DOCUMENTS

| KR | 10-2001-0086457 | 9/2001 |
|---|---|---|
| KR | 10-1738080 | 5/2017 |
| WO | 02-100842 | 12/2002 |

OTHER PUBLICATIONS

Lu et al (Eur. J. Org. Chem. 2007, 676-680). (Year: 2007).*

(Continued)

*Primary Examiner* — Benjamin J Packard
(74) *Attorney, Agent, or Firm* — Meunier Carlin & Curfman LLC

(57) ABSTRACT

The present invention relates to a novel phenylsulfonyl oxazole derivative and a use thereof and specifically, to a compound represented by Chemical Formula 1 in the pres- (Continued)

ent specification or a pharmaceutically acceptable salt thereof, and to a use thereof for prevention, treatment, or improvement of neurodegenerative disease.

10 Claims, 8 Drawing Sheets

Specification includes a Sequence Listing.

(56) References Cited

OTHER PUBLICATIONS

International Search Report (English) and Written Opinion dated Apr. 15, 2019, from International Application No. PCT/KR2019/000373, 15 pages.
Doyle, K.J. et al. "The Rhodium Carbenoid Route to Oxazoles. Synthesis of 4-Functionalised Oxazoles; Three Step Preparation of a Bis-Oxazole", Tetrahedron, vol. 50, No. 12, pp. 3761-3772, 1994.
Lu, L. et al. "I-Catalyzed Reaction of 5-Methoxyoxazoles with Organic Iodides—An Efficient Synthesis of Azalactones", Eur. J. Org. Chem. 2007, 676-680.

* cited by examiner

SEQUENCE LISTING

```
<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: mTNF-alpha Forward

<400> SEQUENCE: 1
gattatggct cagggtccaa                                              20

<210> SEQ ID NO 2
<211> LENGTH: 20
<212> TYPE: DNA
<213> ORGANISM: Artificial Sequence
<220> FEATURE:
<223> OTHER INFORMATION: mTNF-alpha Reverse

<400> SEQUENCE: 2
gctccagtga attcggaaag                                              20

<210> SEQ ID NO 3
<211> LENGTH: 20
<212> TYPE: DNA
<213> ORGANISM: Artificial Sequence
<220> FEATURE:
<223> OTHER INFORMATION: mIL-1beta Forward

<400> SEQUENCE: 3
cccaagcaat acccaaagaa                                              20

<210> SEQ ID NO 4
<211> LENGTH: 20
<212> TYPE: DNA
<213> ORGANISM: Artificial Sequence
<220> FEATURE:
<223> OTHER INFORMATION: mIL-1beta Reverse

<400> SEQUENCE: 4
gcttgtgctc tgcttgtgag                                              20

<210> SEQ ID NO 5
<211> LENGTH: 20
```

```
<212> TYPE: DNA
<213> ORGANISM: Artificial Sequence
<220> FEATURE:
<223> OTHER INFORMATION: mIL-6 Forward

<400> SEQUENCE: 5
ccggagagga gacttcacag                                              20

<210> SEQ ID NO 6
<211> LENGTH: 20
<212> TYPE: DNA
<213> ORGANISM: Artificial Sequence
<220> FEATURE:
<223> OTHER INFORMATION: mIL-6 Reverse

<400> SEQUENCE: 6
ttgccattgc acaactcttt                                              20

<210> SEQ ID NO 7
<211> LENGTH: 20
<212> TYPE: DNA
<213> ORGANISM: Artificial Sequence
<220> FEATURE:
<223> OTHER INFORMATION: mGAPDH Forward

<400> SEQUENCE: 7
tgaatacggc tacagcaaca                                              20

<210> SEQ ID NO 8
<211> LENGTH: 20
<212> TYPE: DNA
<213> ORGANISM: Artificial Sequence
<220> FEATURE:
<223> OTHER INFORMATION: mGAPDH Reverse

<400> SEQUENCE: 8
aggcccctcc tgttattatg                                              20
```

PHENYLSULFONYL OXAZOLE DERIVATIVE AND USE THEREOF

TECHNICAL FIELD

This application claims the priority of Korean Patent Application No. 10-2018-0003586, filed on Jan. 10, 2018, the entirety of which is a reference of the present application.

The present invention relates to a novel phenylsulfonyl oxazole derivative and use thereof and specifically, to a compound represented by Chemical Formula 1 in the present specification or a pharmaceutically acceptable salt thereof, and to a use thereof for prevention, treatment, or improvement of neurodegenerative disease.

BACKGROUND ART

Patients with neurodegenerative disease have abnormalities in a motor control capacity, a cognitive function, a perceptive function, a sensory function, and an autonomic nerve function due to decreased or lost function of nerve cells. During the development of the neurodegenerative disease, abnormal substances are deposited in nerve cells to cause neurotoxicity in many cases. Accordingly, removing these neurotoxicity-causing substances is considered as one approach to the prevention and treatment of the neurodegenerative disease.

On the other hand, in cells, there are systems of degrading and removing metabolites and proteins in the cells, and one of the systems is an ubiquitin-proteasome pathway. Ubiquitin is present in almost all tissues of our body, moves to a proteasome as a protease while attached like a tag to a dead protein, and then destroys and removes the protein attached with the ubiquitin in pieces. The ubiquitin which has been attached to the protein is detached while the protein is degraded and then acts again. Another pathway is autophagy. Autophagosomes fuse with lysosomes to form autophagic lysosomes and substances to be isolated herein are degraded by enzymes of lysosomes (Klionsky, D J and Emr, S D (2000) Autophagy as a regulated pathway of cellular degradation. Science 290, 1717-1721). As a recent autopsy study of the brain of Parkinson's patients, it has been known that vacuoles of autophagy increase in the substantia nigra (Anglade P, Vyas S, Javoy-Agid F, Herrero M T, Michel P P, Marquez J, et al. Apoptosis and autophagy in nigral neurons of patients with Parkinson's disease. Histol Histopathol 1997; 12:25-31). In addition, even in Korean Patent Registration No. 10-1521117, it has been identified that an ideal change in turnover of autophagic vacuoles (AV) is shown in a neurodegenerative disease state such as Alzheimer's disease and abnormal changes occur in which autophagosomes are not degraded but continuously accumulated.

Since autophagy is associated with a wide spectrum of biological processes and various diseases, efforts are being made to find autophagic modulators to develop new compounds having therapeutic effects in related diseases. For example, autophagic modulators comprising natural compounds, compounds known for other uses, or novel compounds or peptides have been developed (Eisenberg, T et al. (2009) Induction of autophagy by spermidine promotes longevity. Nature Cell Biol 11, 1305-1314; Shoji-Kawata, S et al. (2013) Identification of a candidate therapeutic autophagy-inducing peptide. Nature 494, 201-206).

Up to now, there have been many studies on abnormal and reduced autophagy in neurodegenerative diseases such as Alzheimer's disease, and it has been reported that autophagic modulators may be targeted for treatment of Alzheimer's disease, but actually, it is necessary to develop autophagic modulators capable of exhibiting a more significant and safe therapeutic effect by targeting neurodegenerative diseases.

DISCLOSURE

Technical Problem

Therefore, the present inventors completed the present invention by confirming that a compound represented by Chemical Formula 1 was prepared and the compound actually exhibited a significant therapeutic effect by modulating abnormal autophagy shown in neurodegenerative disease in vivo.

Accordingly, an object of the present invention is to provide a compound represented by Chemical Formula 1 below or a pharmaceutically acceptable salt thereof.

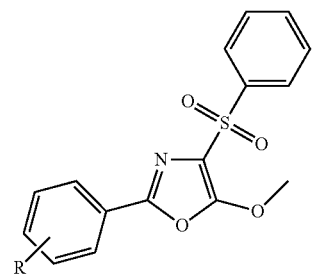

<Chemical Formula 1>

Wherein R is selected from the group consisting of hydrogen, hydroxy, cyano (CN), amino, nitro, substituted or unsubstituted alkyl, substituted or unsubstituted alkenyl, substituted or unsubstituted alkynyl, and substituted or unsubstituted alkoxy.

Another object of the present invention is to provide a pharmaceutical composition for prevention or treatment of neurodegenerative disease comprising the compound represented by Chemical Formula 1 or the pharmaceutically acceptable salt thereof as an active ingredient.

Further, another object of the present invention is to provide a pharmaceutical composition for prevention or treatment of neurodegenerative disease consisting of the compound represented by Chemical Formula 1 or the pharmaceutically acceptable salt thereof.

Further, another object of the present invention is to provide a pharmaceutical composition for prevention or treatment of neurodegenerative disease essentially consisting of the compound represented by Chemical Formula 1 or the pharmaceutically acceptable salt thereof.

Yet another object of the present invention is to provide a food composition for prevention or improvement of neurodegenerative disease comprising the compound represented by Chemical Formula 1 or the pharmaceutically acceptable salt thereof as an active ingredient.

Further, yet another object of the present invention is to provide a food composition for prevention or improvement of neurodegenerative disease consisting of the compound represented by Chemical Formula 1 or the pharmaceutically acceptable salt thereof.

Further, yet another object of the present invention is to provide a food composition for prevention or improvement of neurodegenerative disease essentially consisting of the compound represented by Chemical Formula 1 or the pharmaceutically acceptable salt thereof.

Still another object of the present invention is to provide a method for preparing the compound represented by Chemical Formula 1.

Still yet another object of the present invention is to provide use of the compound represented by Chemical Formula 1 or the pharmaceutically acceptable salt thereof for preparing an agent for prevention or treatment of neurodegenerative disease.

Still yet another object of the present invention is to provide a method for treating neurodegenerative disease characterizing administering an effective dose of a composition comprising the compound represented by Chemical Formula 1 or the pharmaceutically acceptable salt thereof as an active ingredient to a subject in need thereof.

Technical Solution

In order to achieve the objects, the present invention provides a compound represented by Chemical Formula 1 below or a pharmaceutically acceptable salt thereof:

<Chemical Formula 1>

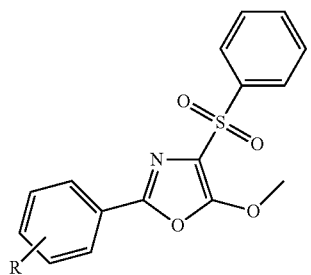

wherein R is selected from the group consisting of hydrogen, hydroxy, cyano (CN), amino, nitro, substituted or unsubstituted alkyl, substituted or unsubstituted alkenyl, substituted or unsubstituted alkynyl, and substituted or unsubstituted alkoxy.

In order to achieve another object of the present invention, the present invention provides a pharmaceutical composition for prevention or treatment of neurodegenerative disease comprising a compound represented by Chemical Formula 1 or a pharmaceutically acceptable salt thereof as an active ingredient.

Further, the present invention provides a pharmaceutical composition for prevention or treatment of neurodegenerative disease consisting of a compound represented by Chemical Formula 1 or a pharmaceutically acceptable salt thereof.

Further, the present invention provides a pharmaceutical composition for prevention or treatment of neurodegenerative disease essentially consisting of a compound represented by Chemical Formula 1 or a pharmaceutically acceptable salt thereof.

In order to achieve yet another object of the present invention, the present invention provides a food composition for prevention or improvement of neurodegenerative disease comprising a compound represented by Chemical Formula 1 above or a pharmaceutically acceptable salt thereof as an active ingredient.

Further, the present invention provides a food composition for prevention or improvement of neurodegenerative disease consisting of a compound represented by Chemical Formula 1 above or a pharmaceutically acceptable salt thereof.

Further, the present invention provides a food composition for prevention or improvement of neurodegenerative disease essentially consisting of a compound represented by Chemical Formula 1 above or a pharmaceutically acceptable salt thereof.

In order to achieve still another object of the present invention, the present invention provides a method for preparing a compound of Chemical Formula 1 above comprising the following steps:

(a) preparing a compound represented by Chemical Formula 4 below by reacting a compound represented by Chemical Formula 2 below and a compound represented by Chemical Formula 3 below;

(b) preparing a compound represented by Chemical Formula 6 below by reacting the compound represented of Chemical Formula 4 below prepared in step (a) and a compound represented by Chemical Formula 5 below; and (c) preparing and obtaining a compound represented by Chemical Formula 1 above by reacting the compound represented of Chemical Formula 6 below prepared in step (b) and a compound represented by Chemical Formula 7 below.

<Chemical Formula 2>

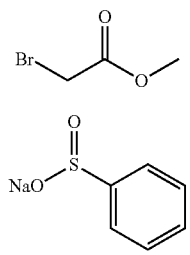

<Chemical Formula 3>

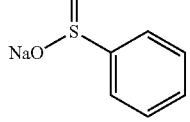

<Chemical Formula 4>

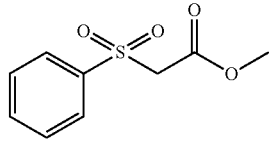

<Chemical Formula 5>

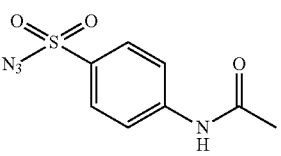

<Chemical Formula 6>

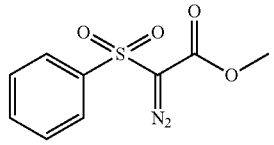

<Chemical Formula 7>

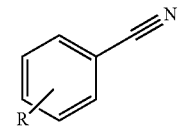

wherein R is selected from the group consisting of hydrogen, hydroxy, cyano (CN), amino, nitro, substituted or unsubstituted alkyl, substituted or unsubstituted alkenyl, substituted or unsubstituted alkynyl, and substituted or unsubstituted alkoxy.

In order to achieve still yet another object of the present invention, the present invention provides use of a compound represented by Chemical Formula 1 above or a pharmaceutically acceptable salt thereof for preparing an agent for prevention or treatment of neurodegenerative disease.

In order to achieve still yet another object of the present invention, the present invention provides a method for treating neurodegenerative disease characterizing administering an effective dose of a composition comprising a compound represented by Chemical Formula 1 above or a pharmaceutically acceptable salt thereof as an active ingredient to a subject in need thereof.

Hereinafter, the present invention will be described in more detail.

The present invention provides a compound represented by Chemical Formula 1 below or a pharmaceutically acceptable salt thereof:

<Chemical Formula 1>

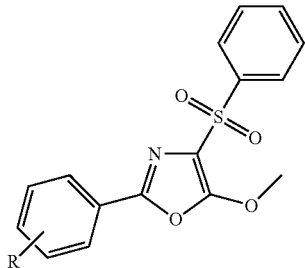

Wherein R is selected from the group consisting of hydrogen, hydroxy, cyano (CN), amino, nitro, substituted or unsubstituted alkyl, substituted or unsubstituted alkenyl, substituted or unsubstituted alkynyl, and substituted or unsubstituted alkoxy.

The following terms in the present invention have meanings defined below unless otherwise indicated. Any term not defined has a meaning to be understood in the art.

In the present invention, 'halogen' refers to fluorine (F), chlorine (Cl), bromine (Br), and iodine (I).

The term 'cyano' used in the present invention refers to a group —CN.

The term 'amino' used in the present invention refers to a primary, secondary or tertiary amino group bonded via a nitrogen atom alone or in combination (wherein, the secondary amino group has an alkyl substituent and the tertiary amino group is defined as having two similar or different alkyl substituents). For example, the 'amino' includes —NH$_2$, methylamino, ethylamino, dimethylamino, diethylamino, methyl-ethylamino, pyrrolidin-1-yl or piperidino, etc., preferably primary amino, and C1-C10 alkylamino.

The term 'nitro' used in the present invention refers to a group —NO$_2$.

The term 'substituted' used in the present invention, unless specified otherwise, refers to at least one substituent, for example, containing one or two or more of a halogen atom, nitro, hydroxy, cyano, amino, thiol, carboxyl, amide, nitrile, sulfide, disulfide, sulphenyl, formyl, formyloxy, or formylamino Unless otherwise specified, or in the case where the structure obtained by such substitution does not significantly adversely affect the properties of the compound represented by Chemical Formula 1 of the present invention, any group or structure described for the compound represented by Chemical Formula 1 of the present invention may be substituted.

The term 'alkyl' used in the present invention, unless otherwise indicated, refers to a hydrocarbon radical of 1 to 10 carbon atoms (C1-C10), more preferably 1 to 6 carbon atoms (C1-C6), much more preferably 1 to 4 carbon atoms (C1-C4), having straight or branched chains. For example, the alkyl may include methyl, ethyl, n-propyl, isopropyl, cyclopropyl, n-butyl, sec-butyl, tert-butyl, cyclobutyl, cyclopropylmethyl, n-pentyl, isopentyl, neopentyl, tert-pentyl, cyclopentyl, cyclobutyl methyl, n-hexyl, isohexyl, cyclohexyl, cyclopentyl methyl, etc. The alkyl may be substituted or unsubstituted alkyl. The substituted alkyl is not limited thereto, but may be preferably trifluoroalkyl.

The term 'alkenyl or alkynyl' used in the present invention refers to a hydrocarbon radical of 2 to 10 carbon atoms, more preferably 2 to 6 carbon atoms, much more preferably 2 to 4 carbon atoms having straight or branched chains containing one or more double or triple bonds. The alkenyl or alkynyl may be substituted or unsubstituted alkenyl or alkynyl, respectively.

The term 'alkoxy' used in the present invention refers to a —O— alkyl group, and the alkyl is as described above. For example, the alkoxy may include methoxy, trifluoromethoxy, ethoxy, n-propoxy, isopropoxy, n-butoxy, t-butoxy, sec-butoxy, n-pentoxy, etc. The alkoxy may be substituted or unsubstituted alkoxy.

Preferably, in the compound of <Chemical Formula 1> of the present invention, R may be one selected from the group consisting of hydrogen, hydroxy, cyano (CN), amino, nitro, halogen-substituted or unsubstituted C1-C4 alkyl, halogen-substituted or unsubstituted C2-C4 alkenyl, halogen-substituted or unsubstituted C2-C4 alkynyl, and halogen-substituted or unsubstituted C1-C4 alkoxy.

More preferably, in the compound of <Chemical Formula 1> of the present invention, R may be trifluoromethyl (—CF$_3$), and a more specific form thereof has a structure represented by <Chemical Formula 1-1> below and may be 5-methoxy-4-(phenylsulfonyl)-2-(4-(trifluoromethyl)phenyl)oxazole.

<Chemical Formula 1-1>

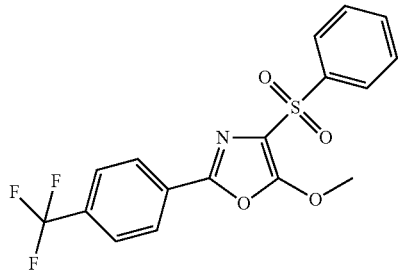

In the present invention, the pharmaceutically acceptable salt refers to a salt or complex of Chemical Formula 1 having a preferable biological activity. Examples of the salt are not limited thereto, but include acid addition salts formed from inorganic acids (e.g., hydrochloric acid, hydrobromic acid, sulfuric acid, phosphoric acid, nitric acid, etc.), and salts formed from organic acids, such as acetic acid, oxalic acid, tartan acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid. The compound may be administered as a pharmaceutically acceptable quaternary salt known to those skilled in the art, particularly, includes chloride, bromide, iodide, —O— alkyl, toluene sulfonate, methyl sulfonate, sulfonate, phosphate, or carbohydrate (e.g., benzoate, succinate, acetate, glycolate, maleate, malate, fumarate, citrate, tartrate, ascorbate, cinnamoate, mandelate, and diphenyl acetate). The compound of Chemical Formula 1 of the present invention may include all salts, hydrates and solvates that can be prepared by general methods, as well as the pharmaceutically acceptable salt.

Further, the compound of the present invention may contain one or more asymmetric carbon atoms, and may exist in a racemic form and an optically active form. All these compounds and diastereomers are included within the scope of the present invention.

The compound of the present invention has a remarkable therapeutic effect, such as reduction of Aβ plaques, improvement in memory and anxiety, and alleviation of neuroinflammation, by modulating abnormal autophagy when applied to neurodegenerative diseases such as Alzheimer's disease. As a result, the compounds of the present application may be very useful for the development of an agent for prevention or treatment of neurodegenerative diseases through the modulation of autophagy. This is well illustrated in the specification examples of the present invention.

Therefore, the present invention provides a pharmaceutical composition for prevention or treatment of neurodegenerative disease comprising a compound represented by Chemical Formula 1 above or a pharmaceutically acceptable salt thereof as an active ingredient.

Further, the present invention provides a pharmaceutical composition for prevention or treatment of neurodegenerative disease consisting of a compound represented by Chemical Formula 1 above or a pharmaceutically acceptable salt thereof.

Further, the present invention provides a pharmaceutical composition for prevention or treatment of neurodegenerative disease essentially consisting of a compound represented by Chemical Formula 1 above or a pharmaceutically acceptable salt thereof.

Further, the present invention provides a food composition for prevention or improvement of neurodegenerative disease comprising a compound represented by Chemical Formula 1 above or a pharmaceutically acceptable salt thereof as an active ingredient.

Further, the present invention provides a food composition for prevention or improvement of neurodegenerative disease consisting of a compound represented by Chemical Formula 1 above or a pharmaceutically acceptable salt thereof.

Further, the present invention provides a food composition for prevention or improvement of neurodegenerative disease essentially consisting of a compound represented by Chemical Formula 1 above or a pharmaceutically acceptable salt thereof.

The neurodegenerative disease may be at least one selected from the group consisting of, for example, Alzheimer's disease, Parkinson's disease, dementia, progressive supranuclear palsy, multi-system atrophy, olive-brain-cerebellar atrophy (OPCA), Shire-Dragger syndrome, striatonigral degeneration, Huntington's disease, amyotrophic lateral sclerosis (ALS), essential tremor, corticobasal degeneration, diffuse Lewy body disease, Parkin's-ALS-dementia complex, pick disease, cerebral ischemia, and cerebral infarction, but is not limited thereto.

The pharmaceutical composition according to the present invention may contain the compound of Chemical Formula 1 or the pharmaceutically acceptable salt thereof alone or may be formulated in a suitable form with a pharmaceutically acceptable carrier, and further contain an excipient or a diluent. The 'pharmaceutically acceptable' generally refers to a non-toxic composition which does not cause an allergic reaction such as gastroenteric trouble and dizziness or a similar reaction thereto, when being physiologically acceptable and administered to the human.

The pharmaceutically acceptable carrier may further include, for example, a carrier for oral administration or a carrier for parenteral administration. The carrier for oral administration may include lactose, starch, cellulose derivatives, magnesium stearate, stearic acid, etc. In addition, the carrier for oral administration may include various drug delivery materials to be used for oral administration to a peptide preparation. In addition, the carrier for parenteral administration may include water, suitable oil, saline, aqueous glucose and glycol, etc., and may further include a stabilizer and a preservative. The suitable stabilizer includes antioxidants such as sodium hydrogen sulfite, sodium sulfite or ascorbic acid. The suitable preservative includes benzalkonium chloride, methyl- or propyl-paraben, and chlorobutanol. The pharmaceutical composition of the present invention may further include a lubricant, a wetting agent, a sweetening agent, a flavoring agent, an emulsifying agent, a suspending agent, and the like in addition to the above ingredients.

The composition of the present invention may be administered to mammals including humans even by any method. For example, the composition may be administered orally or parenterally. The parenteral administration method is not limited thereto, but for example, may be injection or infusion by intravenous, intraperitoneal, intracerebral, subcutaneous, intramuscular, intraocular, intraarterial, intrathecal, intramedullary, intradural, intracardiac, transdermal, subcutaneous, intranasal, intestinal, topical, sublingual, intrarectal or intralesional route, or injection or infusion by a sustained release system to be described below. For example, the compound of Chemical Formula 1 above may be administered systemically or locally.

The pharmaceutical composition of the present invention may be formulated as a preparation for oral administration or parenteral administration according to the administration route as described above.

In the case of the preparation for oral administration, the composition of the present invention may be formulated as powders, granules, tablets, pills, sugarcoated pills, capsules, liquids, gels, syrups, slurries, suspensions, etc. by using methods known in the art. For example, the preparation for oral administration may be obtained as tablets or sugarcoated pills by mixing an active ingredient with a solid excipient, grinding the mixture, and then adding a suitable adjuvant to be processed as a granular mixture. An example of the suitable excipient may include fillers, such as sugars including lactose, dextrose, sucrose, sorbitol, mannitol, xylitol, erythritol, maltitol, etc., starches including corn starch, wheat starch, rice starch, potato starch, etc., celluloses including cellulose, methyl cellulose, sodium carboxymethylcellulose, hydroxypropylmethyl-cellulose, etc., gelatin, and polyvinylpyrrolidone. In addition, in some cases, crosslinked polyvinylpyrrolidone, agar, alginic acid, sodium alginate, or the like may be added as a disintegrant. In addition, the pharmaceutical composition of the present invention may further include an anti-coagulating agent, a lubricant, a wetting agent, a fragrance, an emulsifier, and a preservative.

The preparation for parenteral administration may be formulated by methods known in the art in the form of injections, creams, lotions, external ointments, oils, moisturizers, gels, aerosols and nasal inhalants. These formulations may include all formulations commonly known in all pharmaceutical chemistry.

A total effective dose of the composition of the present invention may be administered to a patient in a single dose, or may be administered in a multiple dose for a long period of time by a fractionated treatment protocol. In the pharmaceutical composition of the present invention, the content of the active ingredient may vary depending on the severity of disease. Preferably, a preferred total dose of the pharmaceutical composition of the present invention may be about 1 ng to 10 mg, most preferably 1 μg to 1 mg per day, when the patient's body weight is typically 60 kg. However, the effective dose of the pharmaceutical composition to the patient is determined by considering various factors, such as the age, body weight, health conditions, and gender of a patient, the severity of disease, diet, and excretion rate, as well as a formulation method, an administration route and the number of treatment times. Accordingly, considering such an aspect, those skilled in the art may determine a suitable effective dose of the composition of the present invention. The pharmaceutical composition according to the present invention is not particularly limited to the formulation, the administration route, and the administration method thereof, as long as the effects of the present invention are shown.

Meanwhile, the compound according to the present invention can be formulated in various forms depending on the purpose. Preparation Examples for the composition of the present invention are illustrated below.

<Preparation Example 1> Preparation of Pharmaceutical Formulation

1. Preparation of Powder
Compound of Chemical Formula 1 according to the present invention 2 g
 Lactose 1 g
The ingredients were mixed and filled in an airtight fabric to prepare a powder.

2. Preparation of Tablet
Compound of Chemical Formula 1 according to the present invention 100 mg
 Corn starch 100 mg
 Lactose 100 mg
 Magnesium stearate 2 mg
The ingredients were mixed and then tableted according to a general tablet preparation method to prepare a tablet.

3. Preparation of Capsule
Compound of Chemical Formula 1 according to the present invention 100 mg
 Corn starch 100 mg
 Lactose 100 mg
 Magnesium stearate 2 mg
The ingredients were mixed and then filled in a gelatin capsule according to a general capsule preparation method to prepare a capsule.

4. Preparation of Pill
Compound of Chemical Formula 1 according to the present invention 1 g
 Lactose 1.5 g
 Glycerin 1 g
 Xylitol 0.5 g
The ingredients were mixed and then prepared to be 4 g per pill according to a general method.

5. Preparation of Granules
Compound of Chemical Formula 1 according to the present invention 150 mg
 Soybean extract 50 mg
 Glucose 200 mg
 Starch 600 mg
The ingredients were mixed, added with 100 mg of 30% ethanol, and dried at 60° C. to form granules, and then the formed granules were filled into a fabric.

The food composition according to the present invention includes all types of functional foods, nutritional supplements, health foods, and food additives. These types may be prepared in various forms according to general methods known in the art.

For example, as the health foods, the food composition itself of the present invention may be prepared and drunk in the form of tea, juice, and drink or granulated, encapsulated, and powdered to be taken. In addition, the food composition of the present invention may be mixed with a known substance or active ingredient known to have an effect for prevention, improvement, or treatment on neurodegenerative disease to be prepared in the form of a composition.

Further, the functional foods may be prepared by adding the food composition of the present invention to beverages (including alcoholic beverages), fruits and processed foods thereof (e.g., canned fruits, bottled fruits, jams, marmalade, etc.), fish, meat, and processed foods thereof (e.g., ham, sausage corn beef, etc.), breads and noodles (e.g., udon, buckwheat noodles, ramen, spaghetti, macaroni, etc.), juice, various drinks, cookies, syrup, dairy products (e.g., butter, cheese, etc.), edible plant oils, margarine, vegetable proteins, retort foods, frozen foods, various seasonings (e.g., soybean paste, soy sauce, sauces, etc.), etc.

For example, like general drinks, a health drink composition may contain various flavoring agents or natural carbohydrates as an additional ingredient. The above-mentioned natural carbohydrates include monosaccharides such as glucose and fructose, disaccharides such as maltose and sucrose, polysaccharides such as dextrin and cyclodextrin, and sugar alcohols such as xylitol, sorbitol and erythritol. As the sweetening agent, natural sweetening agents such as thaumatin and stevia extract, synthetic sweetening agents such as saccharin and aspartame, or the like may be used. A ratio of the natural carbohydrates may be generally about 0.01 g to 0.20 g, preferably about 0.04 g to 0.10 g per 100 g of the composition of the present invention.

In addition to the ingredients, the composition of the present invention may contain various nutrients, vitamins, electrolytes, flavoring agents, coloring agents, pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, or the like. Besides, the composition of the present invention may contain pulps for preparing natural fruit juices, fruit juice beverages, and vegetable beverages. These ingredients may be used independently or in combination. Although the ratio of the additives is not very important, generally, the ratio is selected in a range of 0.01 to 0.20 part by weight per 100 parts by weight of the composition of the present invention.

The preferred content of the compounds in the food composition according to the present invention is not limited thereto, but is preferably from 0.01 to 50 wt % of the total weight of the food finally produced. In order to use the food composition of the present invention in the form of food additives, the food composition may be prepared and used in the form of powders or concentrates.

The present invention also provides a method for preparing the compound of Chemical Formula 1 above, comprising the following steps:

(a) preparing a compound represented by Chemical Formula 4 below by reacting a compound represented by Chemical Formula 2 below and a compound represented by Chemical Formula 3 below;

(b) preparing a compound represented by Chemical Formula 6 below by reacting the compound represented of Chemical Formula 4 below prepared in step (a) and a compound represented by Chemical Formula 5 below; and (c) preparing and obtaining the compound represented by Chemical Formula 1 above by reacting the compound represented of Chemical Formula 6 below prepared in step (b) and a compound represented by Chemical Formula 7 below.

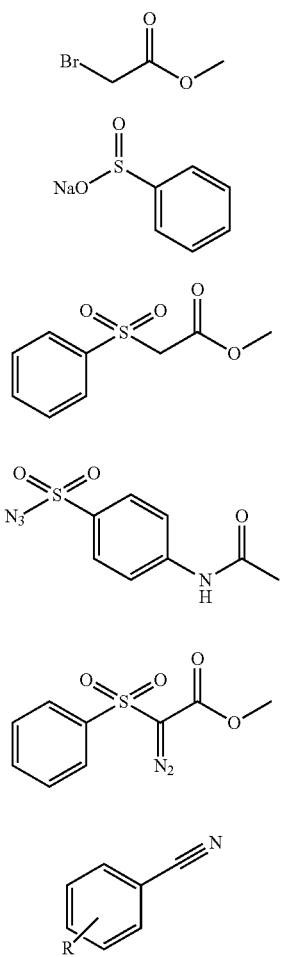

<Chemical Formula 2>

<Chemical Formula 3>

<Chemical Formula 4>

<Chemical Formula 5>

<Chemical Formula 6>

<Chemical Formula 7>

Wherein R is selected from the group consisting of hydrogen, hydroxy, cyano (CN), amino, nitro, substituted or unsubstituted alkyl, substituted or unsubstituted alkenyl, substituted or unsubstituted alkynyl, and substituted or unsubstituted alkoxy.

The solvent used in steps (a) to (c) of the present invention is not particularly limited as long as it is a solvent that dissolves a starting material and does not inhibit the reaction. For example, the solvent may use ether-based solvents such as tetrahydrofuran, 1,2-dimethoxyethane, diethyl ether or dioxane; aromatic hydrocarbon-based solvents such as benzene, toluene or xylene; aliphatic hydrocarbon-based solvents such as dichloromethane, chloroform, dichloroethane, trichloroethane, tetrachloroethane, dichloroethylene, trichloroethylene, and tetrachloroethylene; amide-based solvents such as N,N-dimethylformamide, N,N-dimethylacetamide or N-methylpyrrolidone; nitrile-based solvents such as acetonitrile, propionitrile, butyronitrile, and valeronitrile; organic solvents such as dimethyl sulfoxide; alcohol-based solvents such as methanol, ethanol, propanol, n-butanol or t-butanol; or mixtures thereof or a mixed solvent of the solvent and water. The preferred type of solvent to be used in the reaction of each step can be appropriately selected and used by those skilled in the art according to the nature of the solvent by referring to the embodiments of the present specification.

The conditions such as a reaction temperature, a reaction time, and an amount of reaction raw materials in each step are not particularly limited, and can be set by appropriately selecting conditions under which the reaction may be sufficiently performed by those skilled in the art according to a desired synthesis rate and a process effect.

After the reaction in each step, the solvent used for the reaction is distilled and then subjected to a general post-treatment process such as washing, drying and purification to obtain a high-purity compound.

The present invention provides use of the compound represented by Chemical Formula 1 above or a pharmaceutically acceptable salt thereof for preparing an agent for prevention or treatment of neurodegenerative disease.

The present invention provides a method for treating neurodegenerative disease characterizing administering an effective dose of a composition comprising the compound represented by Chemical Formula 1 above or a pharmaceutically acceptable salt thereof as an active ingredient to a subject in need thereof.

The term 'effective dose' of the present invention refers to an amount which exhibits effects for improving, treating, preventing, detecting, diagnosing or inhibiting of neurodegenerative disease when administered to the subject. The 'subject' may be animals, preferably, mammals, particularly animals including humans and may also be cells, tissues, and organs derived from animals. The subject may be a patient requiring the effects.

The term 'treatment' of the present invention comprehensively refers to improving neurodegenerative disease or symptoms of the neurodegenerative disease, and may include treating or substantially preventing the disease, or improving the condition thereof and includes alleviating, treating or preventing a symptom or most of symptoms derived from the neurodegenerative disease, but is not limited thereto.

The term 'comprising' of the present invention is used in the same manner as 'containing' or 'characterizing', and does not exclude additional ingredients or steps of the method which are not mentioned in the composition or the method. The term 'consisting of' means excluding additional elements, steps or ingredients, etc., which are not separately described. The term 'essentially consisting of' means including ingredients or steps that do not substantially affect basic properties thereof in addition to the described ingredients or steps within the scope of the composition or the method.

Advantageous Effects

The compounds of the present invention have a remarkable therapeutic effect, such as reduction of Aβ plaques, alleviation of neuroinflammation, and improvement in memory and anxiety, by modulating abnormal autophagy when applied to neurodegenerative disease such as Alzheimer's disease. Therefore, the compounds of the present application may be very useful for the development of an agent for prevention or treatment of neurodegenerative disease through the modulation of autophagy.

DESCRIPTION OF DRAWINGS

FIG. 5A illustrates results of evaluating learning and memory through a Morris water maze test in a wild type mouse (n=6), an APP/PS1 mouse injected with PBS (n=6), and an APP/PS1 mouse injected with an autophagy enhancing compound (n=10).

FIG. 5B illustrates a result showing a time left in a target platform on day 11 of the test.

FIG. 5C illustrates the number of times of entering into a target area of the target platform on day 11 of the test.

FIG. 5D illustrates results of contextual and tone tasks during a fear conditioning test.

FIG. 6A illustrates a result of quantifying areas of astrocytes (GFAP) through immunofluorescence staining in the brain cortices and the hippocampi of a wild type mouse (WT), an APP/PS1 mouse injected with PBS, and an APP/PS1 mouse injected with an autophagy enhancing compound.

FIG. 6B illustrates a result of quantifying areas of microglia (Iba-1) through immunofluorescence staining in the brain cortices and the hippocampi of a wild type mouse (WT), an APP/PS1 mouse injected with PBS, and an APP/PS1 mouse injected with an autophagy enhancing compound.

FIG. 6C illustrates a result of evaluating mRNA expression levels of inflammatory markers TNF-α, IL-1β, and IL-6 in the brain cortices and the hippocampi of a wild type mouse (WT), an APP/PS1 mouse injected with PBS, and an APP/PS1 mouse injected with an autophagy enhancing compound.

MODE FOR INVENTION

Figure 1:
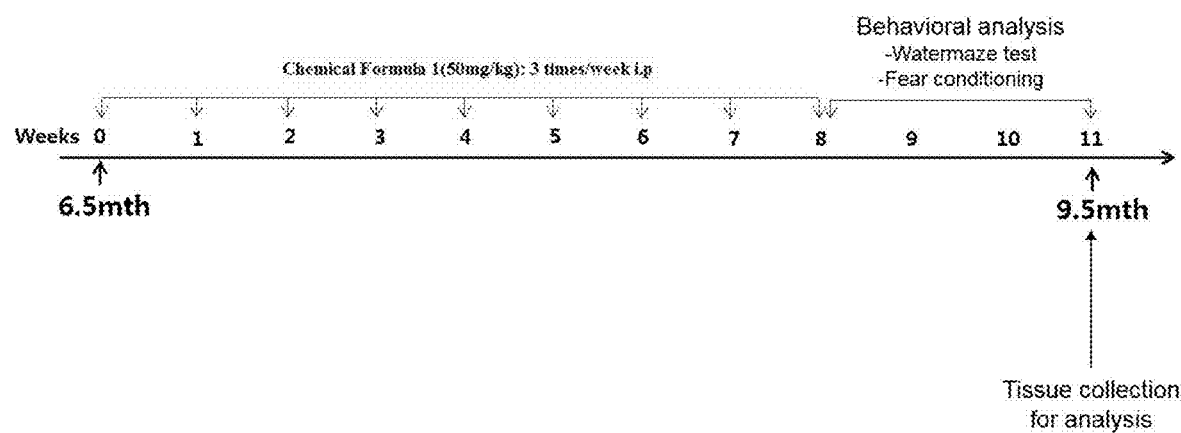
FIG. 1 is a view illustrating an outline of an experiment performed to determine an effect of an autophagy enhancing compound on Alzheimer's disease.

Hereinafter, the present invention will be described in detail.

However, the following Examples are just illustrative of the present invention, and the contents of the present invention are not limited to the following Examples.

Example 1: Preparation of Compounds

Compounds corresponding to Chemical Formula 1 of the present invention were obtained by the following methods.

1-1. Preparation of 5-methoxy-4-(phenylsulfonyl)-2-(4-(trifluoromethyl)phenyl)oxazole 2-(2-chlorophenyl)-5-methoxy-4-(phenylsulfonyl)oxazole was prepared by the following steps (1) to (3).

(1) Step 1: Preparation of methyl 2-(phenylsulfonyl)acetate

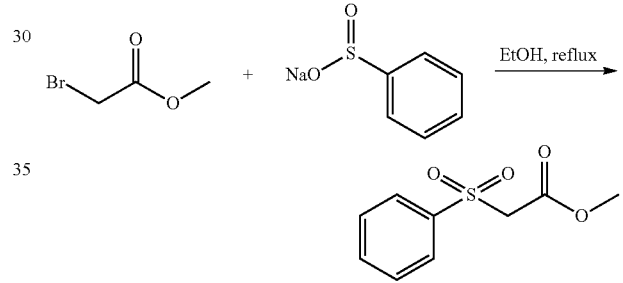

A solution of methyl bromoacetate (10 g, 65.38 mmol), benzenesulfinic acid and sodium salt (12.9 g, 78.4 mmol) mixed in ethanol (200 mL) was refluxed for 24 hours. Next, the excess solvent was removed under reduced pressure. Next, the reaction mixture was dissolved in dichloromethane (400 mL) and washed with water (2×200 mL) and brine (salt water, 50 mL). Next, an organic layer was dried in anhydrous Na$_2$SO$_4$ and concentrated under reduced pressure to obtain methyl 2-(phenylsulfonyl)acetate (13.5 g, 96%). The obtained compound was used for synthesis of a compound in a next step without a separate purification process.

(2) Step 2: Preparation of methyl 2-diazo-2-(phenylsulfonyl)acetate

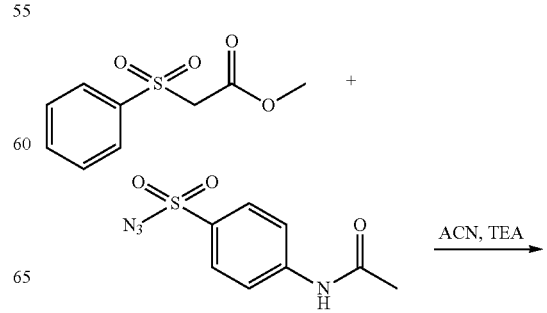

-continued

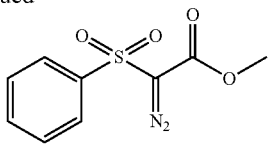

Triethylamine (7.0 g, 69.3 mmol) was added in a solution stirred with methyl 2-(phenylsulfonyl)acetate (13.5 g, 67.7 mmol) and 4-acetamidobenzenesulfonyl azide (16.65 g, 69.31 mmol) in acetonitrile (500 mL) at 0° C. Thereafter, the reaction mixture was stirred at room temperature for 24 hours, the reaction mixture was concentrated under reduced pressure, and the produced precipitate was stirred in a solution of ethyl acetate and n-hexane diluted at 1:1 (3×600 mL, 1:1 ethyl acetate:n-hexane), and then the mixed organic material was concentrated under reduced pressure. Thereafter, the mixture was purified by a column chromatography using ethyl acetate and n-hexane to obtain 15 g of a methyl 2-diazo-2-(phenylsulfonyl)acetate compound as a lemon yellow solid (99%).

(3) Step 3: Preparation of 5-methoxy-4-(phenylsulfonyl)-2-(4-(trifluoromethyl)phenyl) oxazole

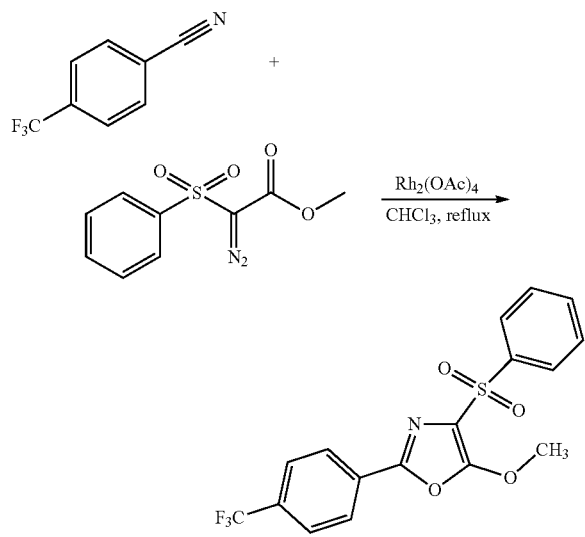

Methyl 2-diazo-2-(phenylsulfonyl)acetate (1.85 g, 7.71 mmol) was added to a solution in which 4-(trifluoromethyl) benzonitrile (1.2 g, 7.013 mmol) and rhodium (II) acetate (61.99 mg, 0.14 mmol) were refluxed in chloroform (20 ml). After addition, the reaction mixture was refluxed for 3 hours. The reaction mixture was concentrated under reduced pressure to obtain 1.5 g of 5-methoxy-4-(phenylsulfonyl)-2-(4-(trifluoromethyl)phenyl)oxazole as a white solid using a column chromatography (56%).

1H NMR (300 MHz, DMSO-d6): δ 8.06 (d, J=8.28 Hz, 2H), 7.95 (d, J=7.18 Hz, 2H), 7.88 (d, J=8.28 Hz, 2H), 7.76-7.61 (m, 3H), 4.30 (s, 3H).

Example 2: Confirmation of Effects for Prevention and Treatment on Neurodegenerative Disease Experiment Method 1. Mouse and Experiment Outline A mouse experiment was approved by the Kyungpook National University Institutional Animal Care and Use Committee (IACUC). As an animal model of neurodegenerative disease (particularly, Alzheimer's disease), a transgenic mouse line overexpressing APPswe (hAPP695swe) and PS1 (presenilin-1M146V) based on a C57BL/6 mouse (Charles River, UK) was used. [hereinafter, APP/PS1 mouse (denoted by AD), GlaxoSmithKline Co., Ltd.]

To confirm a therapeutic effect of the autophagy enhancing compound obtained in <Example 1>, an experimental substance was administered to the animal model according to the experimental outline (schedule) illustrated in FIG. 1. Specifically, PBS or the autophagy enhancing compound was intraperitoneally injected into a 6.5-month-old mouse 3 times a week at a dose of 50 mg/kg. After two months of the injection of the autophagy enhancing compound, behavioral analysis was performed, and the brain tissue of the mouse was used as a sample after the behavioral analysis (i.e., at 9.5 weeks old of mouse) (see FIG. 1).

2. Immunofluorescence

After immobilization of the mouse's cerebrum and hippocampus, 0.5% thioflavin S (Sigma-Aldrich), anti-20G10 against Aβ42 (mouse, 1:1000) and anti-G30 against A1340 (rabbit, 1:1000), anti-GFAP (rabbit, 1:500, DAKO) and anti-Iba-1 (rabbit, 1:500, WAKO) were incubated together. The sites were analyzed using a confocal laser scanning microscope or an Olympus BX51 microscope equipped with Fluoview SV1000 imaging software (Olympus FV1000, Japan). A percentage of an area of a stained area to an area of total tissues was quantified and analyzed by using Metamorph software (Molecular Devices).

3. Real-Time Quantitative PCR

A real-time quantitative PCR method was used to measure the expression levels of inflammatory response-related cytokines (TNF-α, IL-1β, and IL-6). Total RNA was extracted from the brain tissue using an RNeasy Plus mini kit (Qiagen, Korea, Ltd), and cDNA was synthesized from a total of 5 μg of RNA using a kit from Clontech (Mountain View, Calif.). In addition, by using a Corbett research RG-6000 real-time PCR instrument, real-time quantitative PCR was performed by setting 95° C., 10 minutes; 95° C., 10 seconds; and 58° C., 15 seconds as one cycle and repeating 40 cycles. Primer pairs used in the real-time quantitative PCR are shown in Table 1.

TABLE 1

| | | | |
|---|---|---|---|
| mTNF-α | Forward | 5'-GAT TAT GGC TCA GGG TCC AA-3' | SEQ ID NO: 1: |
| | Reverse | 5'-GCT CCA GTG AAT TCG GAA AG-3' | SEQ ID NO: 2: |
| mIL-1β | Forward | 5'-CCC AAG CAA TAC CCA AAG AA-3' | SEQ ID NO: 3: |
| | Reverse | 5'-GCT TGT GCT CTG CTT GTG AG-3' | SEQ ID NO: 4: |
| mIL-6 | Forward | 5'-CCG GAG AGG AGA CTT CAC AG-3' | SEQ ID NO: 5: |
| | Reverse | 5'-TTG CCA TTG CAC AAC TCT TT-3' | SEQ ID NO: 6: |
| mGAPDH | Forward | 5'-TGA ATA CGG CTA CAG CAA CA-3' | SEQ ID NO: 7: |
| | Reverse | 5'-AGG CCC CTC CTG TTA TTA TG-3' | SEQ ID NO: 8: |

4. Western Blot

Expression of the following genes was analyzed using Western blotting. First, antibodies against LC3, beclin-1, and p62 [all, purchased from cell signaling Technologies], cathepsin D (R&D systems) and β-actin (Santa Cruz) were used, and density quantification was performed by using ImageJ software (US National Institutes of Health).

5. Behavioral Experiment

In order to confirm potential effects on learning and memory, Morris water maze (MWM) and fear conditioning tests were performed. In the MWM, the mouse learned a task 4 times a day for 10 days, a platform was removed on day 11, and a probe trial was performed. In the fear conditioning, on the first day, the mouse was placed in a conditioning chamber, and sound stimulation (10 kHz, 70 dB) and electrical stimulation (0.3 mA, 1 s) were given. On the second day, the memory on a space was confirmed without stimulation in the same conditioning chamber as the first day, and on the third day, the memory test for fear was performed when only the sound stimulation was given in another conditioning chamber.

6. Statistical Analysis

For comparison of two groups, a T-test of a student was performed, while for comparison of multiple groups, repeated measurement analysis of a Tukey's HSD test and a variance test was performed according to an SAS statistical package (release 9.1; SAS Institute Inc., Cary, N.C.). *$p<0.05$ and **$p<0.01$ were considered to be significant.

Experimental Results

1. Confirmation of Reduction of Amyloid-β Deposition in APP/PS1 Mouse Injected with Autophagy Enhancing Compound In order to determine whether the aforementioned autophagy enhancing compound had effects for prevention and treatment on neurodegenerative disease, the effect of the compound on an Alzheimer's model was representatively evaluated. Among the autophagy enhancing compounds obtained in Example 1, 5-methoxy-4-(phenylsulfonyl)-2-(4-(trifluoromethyl)phenyl)oxazole (Example 1-1) was typically used, and in the same manner as shown in FIG. 1, the autophagy enhancing compound was administered intraperitoneally to an Alzheimer's animal model for 2 months and the results were evaluated.

First, an amyloid-β (Aβ) profile of an Alzheimer's lesion and the deposition degree of tau protein were confirmed. First, the cerebral cortex and hippocampus regions of the mouse were stained with thioflavin S (ThioS) according to a known method to confirm the deposition degree of fibrillar amyloid-β. In addition, immunofluorescence staining of Aβ40, Aβ42, and AT8 was performed to confirm the deposition degree of amyloid-β and tau protein.

Figure 2:
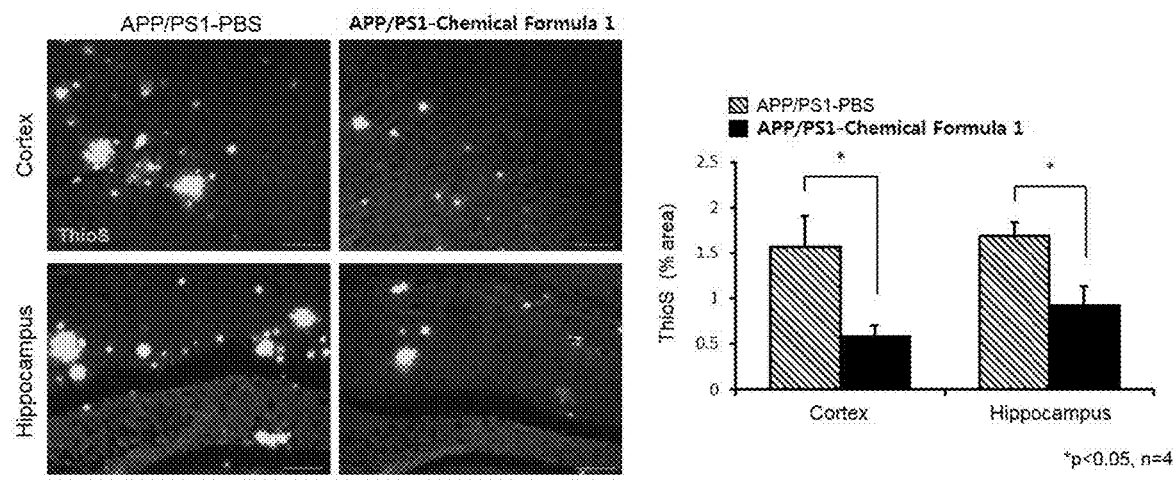
FIG. 2 illustrates a result of immunofluorescence staining of thioflavin S (ThioS, fibrillar amyloid beta plaques) in the brain cortex and the hippocampus of an APP/PS1 mouse injected with PBS or an autophagy enhancing compound and a result of quantifying areas occupied with the fibrillar amyloid beta plaques (n=4/group) (APP/PS1: Alzheimer's animal model).
Figure 3A:
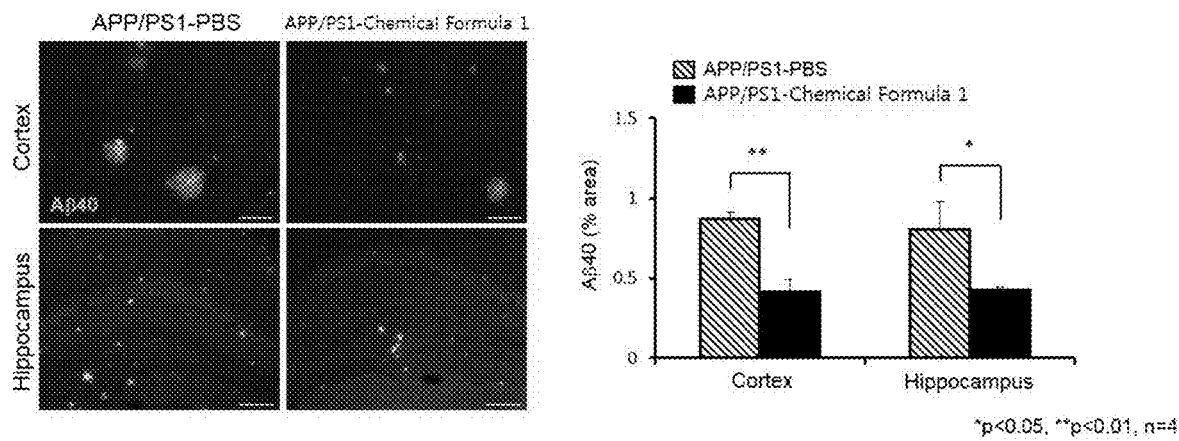
FIGS. 3A and 3B illustrate results of immunofluorescence staining and quantification of accumulation of Aβ40 (FIG. 3A) or Aβ42 (FIG. 3B) in the brain cortex and the hippocampus of an APP/PS1 mouse injected with PBS or an autophagy enhancing compound (n=4/group) (APP/PS1: Alzheimer's animal model).
Figure 3B:
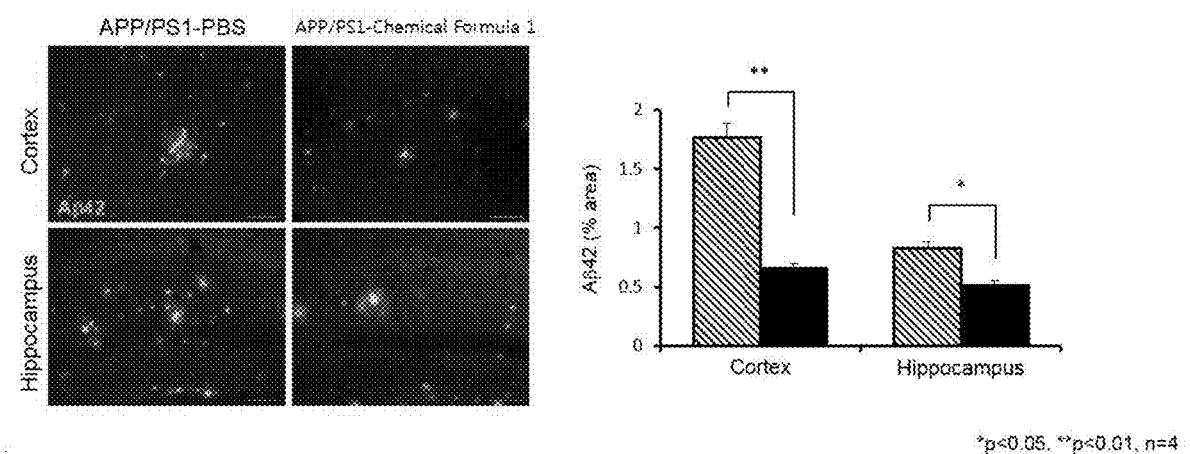
Figure 4:
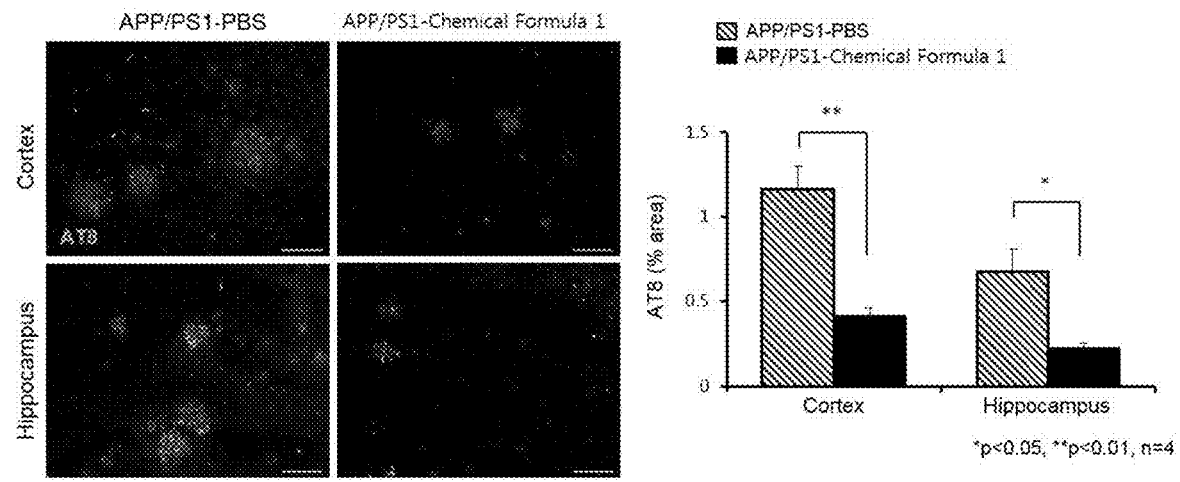
FIG. 4 illustrates results of immunofluorescence staining and quantification of accumulation of tau protein (AT8) in the brain cortex and the hippocampus of an APP/PS1 mouse injected with PBS or an autophagy enhancing compound (n=4/group) (APP/PS1: Alzheimer's animal model)

As a result of the experiment, compared to the APP/PS1 mouse, the deposition of fibrillar Aβ (see FIG. 2) and the deposition of Aβ40 and Aβ42 (see FIGS. 3A and 3B) and tau protein (see FIG. 4) in an APP/PS1 mouse injected with the autophagy enhancing compound were confirmed to be significantly low.

2. Confirmation of Improvement of Learning and Cognition in APP/PS1 Mouse Injected with Autophagy Enhancing Compound To determine potential effects of an autophagy enhancing compound on learning and cognition in an Alzheimer's animal, Morris water maze (MWM) and fear conditioning tests were performed.

Figure 5A:
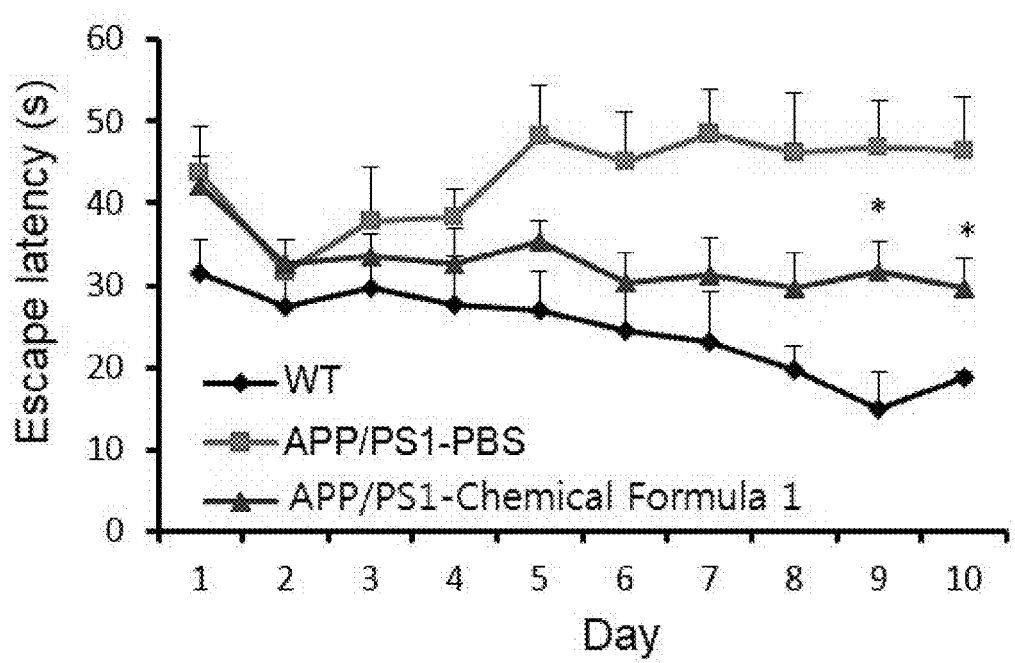
FIGS. 5A to 5D illustrate results showing that the injection of an autophagy enhancing compound in an APP/PS1 mouse restores learning and cognitive functions (WT: wild type, APP/PS1: Alzheimer's animal model).
Figure 5B:
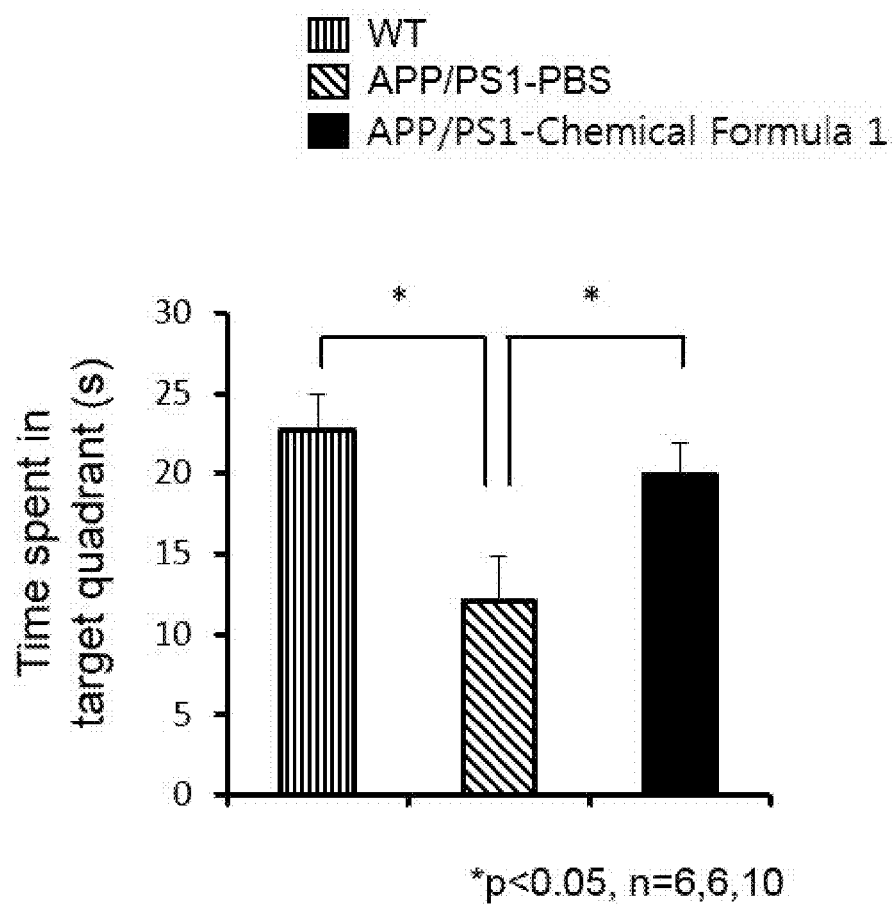
Figure 5C:
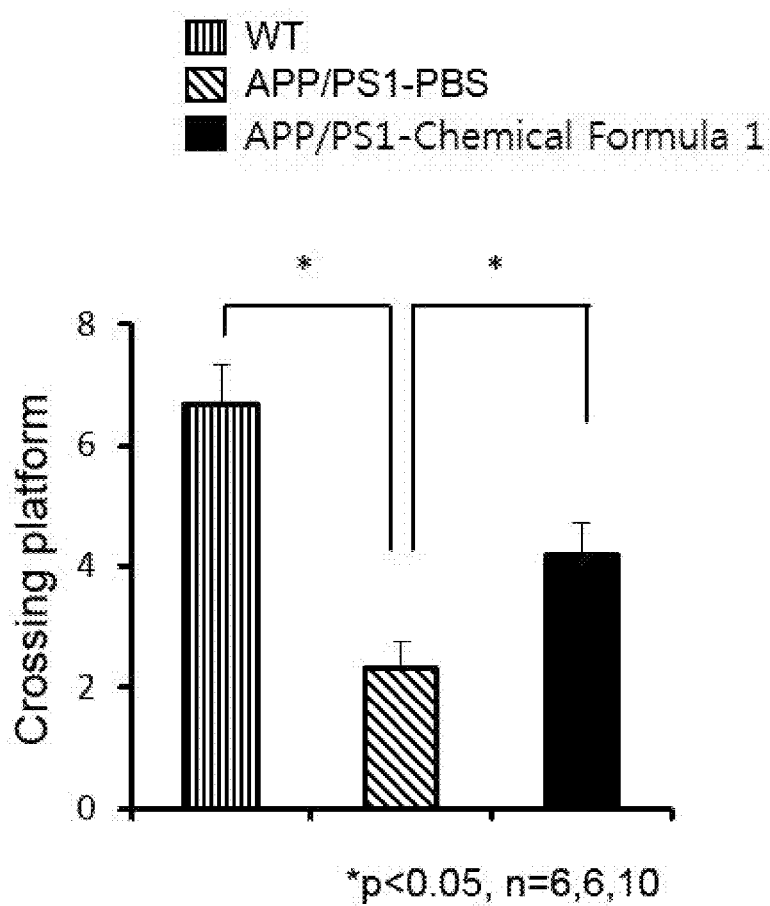
Figure 5D:
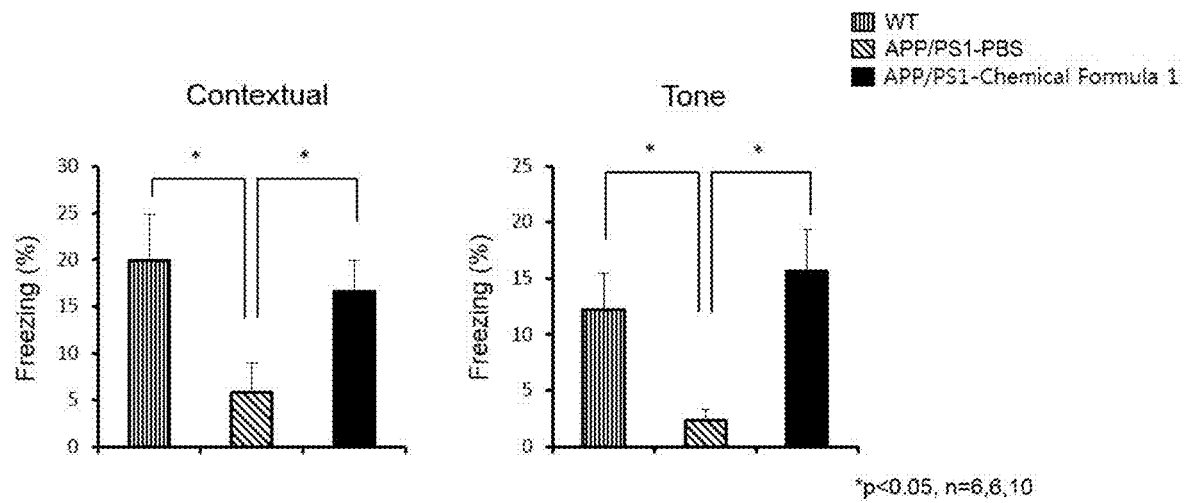

As illustrated in FIGS. 5A to 5C, the APP/PS1 mouse showed severe impairment in spatial memory, cognition and memory formation, but it was confirmed that in the APP/PS1 mouse injected with the autophagy enhancing compound, such impairment was significantly improved (FIGS. 5A to 5C). In addition, it was confirmed that the autophagy enhancing compound showed a remarkable memory improvement effect even in the fear conditioning test (FIG. 5D).

3. Confirmation of Neuroinflammatory Change in APP/PS1 Mouse Injected with Autophagy Enhancing Compound In order to confirm an effect of the injection of the autophagy enhancing compound on a neuroinflammatory change in an Alzheimer's animal, the present inventors observed changes in astrocytes (using GFAP as a marker) and microglia (using Iba-1 as a marker) in the brain.

Figure 6A:
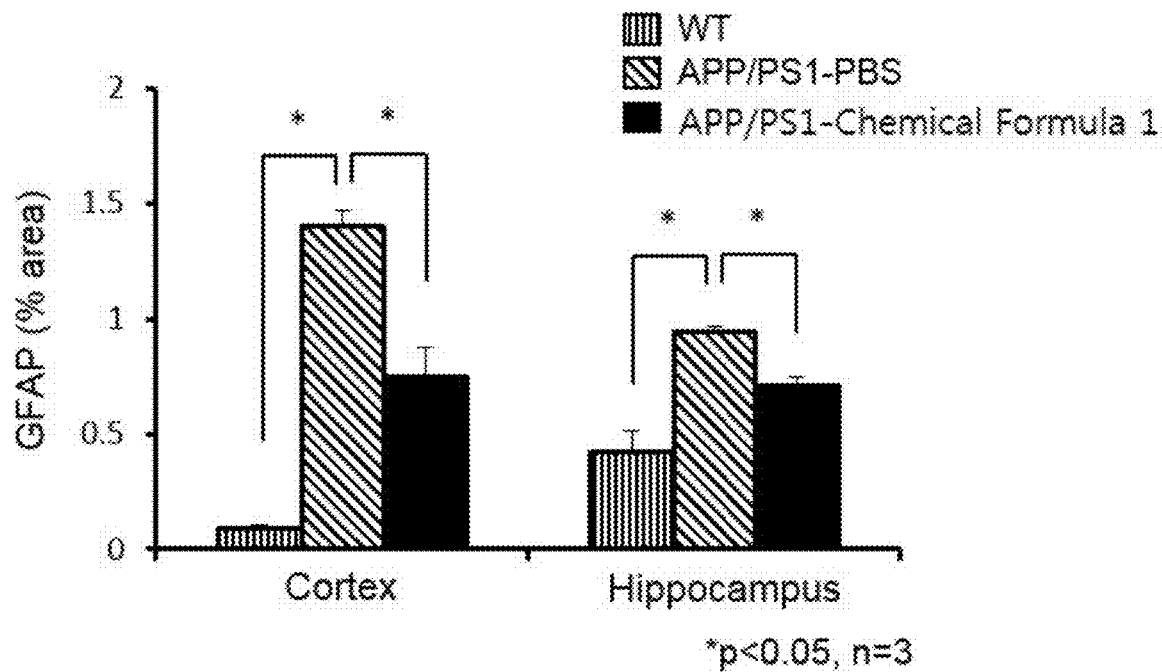
FIGS. 6A to 6C illustrate results of confirming that the increased neuroinflammation in an APP/PS1 mouse is reduced by the injection of the autophagy enhancing compound (n=3/group).
Figure 6B:
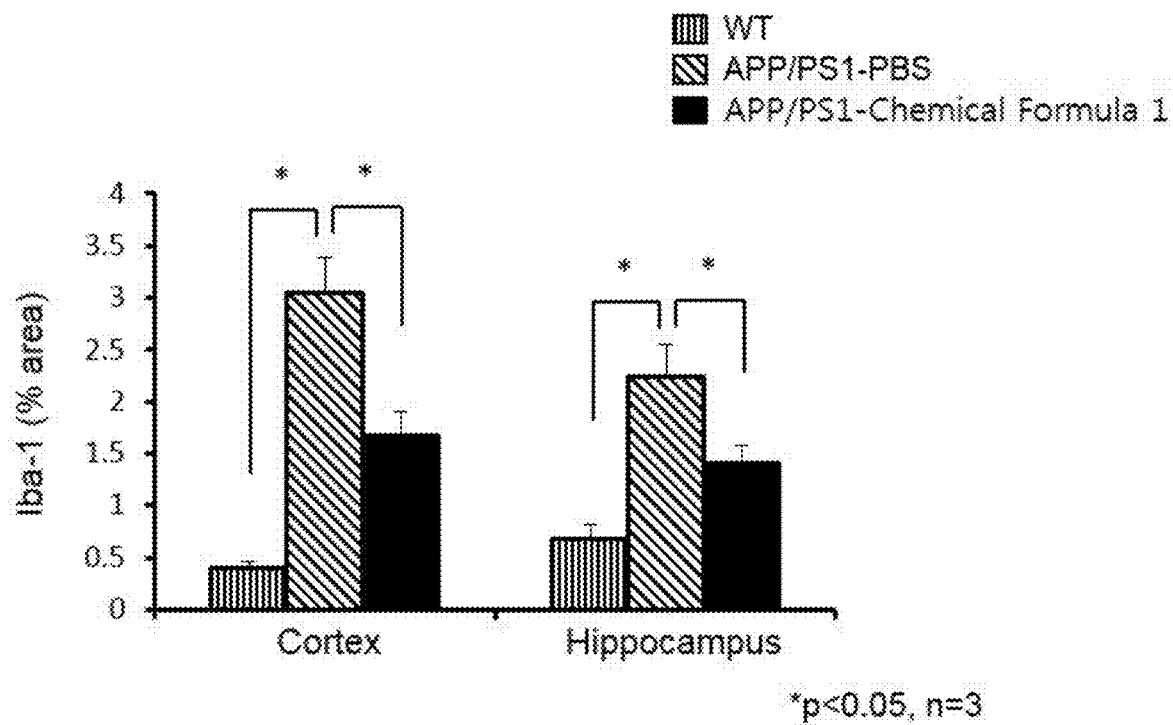
Figure 6C:
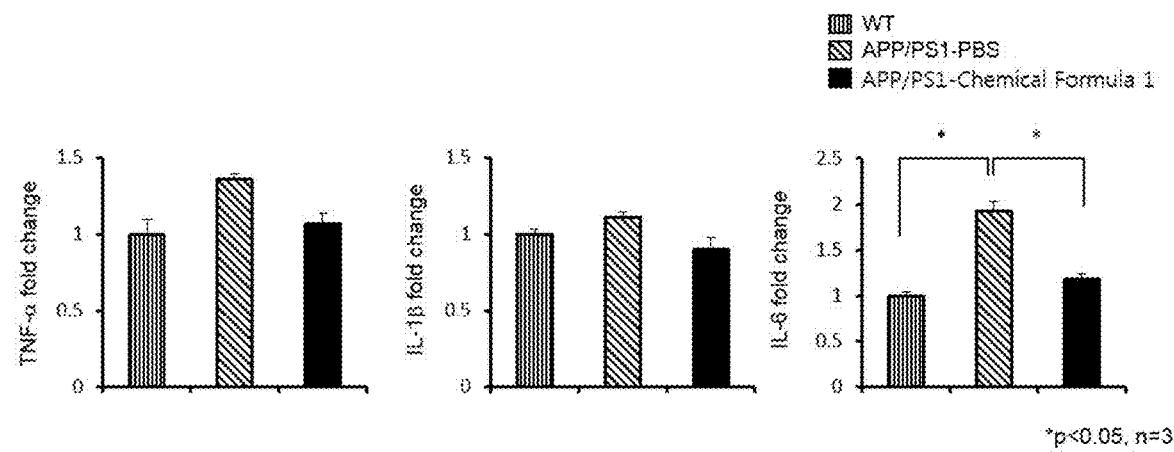

As a result of the experiment, compared with the APP/PS1 mouse, it was confirmed that the activities of astrocytes and microglia were significantly reduced in the APP/PS1 mouse injected with the autophagy enhancing compound (FIGS. 6A and 6B). In addition, in the APP/PS1 mouse, the gene expression of inflammatory cytokines TNF-α, IL-1β and IL-6 was significantly increased compared to a wild mouse, but in the APP/PS1 mouse injected with the autophagy enhancing compound, it was confirmed that the expression of the inflammatory cytokines was restored to a normal level (FIG. 6C). Through these results, it was confirmed that the injection of the autophagy enhancing compound modulated a neuroinflammatory response in an Alzheimer's brain environment.

4. Confirmation of Effect on Autophagy-Related Genes in APP/PS1 Mouse Injected with Autophagy Enhancing Compound In order to confirm how the aforementioned autophagy enhancing compound (in particular, 5-methoxy-4-(phenylsulfonyl)-2-(4-(trifluoromethyl)phenyl)oxazole) actually act in an autophagy-related pathway in vivo, conversion of LC3-I to LC3-II, and expression levels of beclin-1, cathepsin D and p62 were confirmed through a Western blotting experiment in brain tissue samples of 9.5-month-old WT, APP/PS1 (untreated group), and an APP/PS1 mouse injected with the autophagy enhancing compound.

Figure 7:
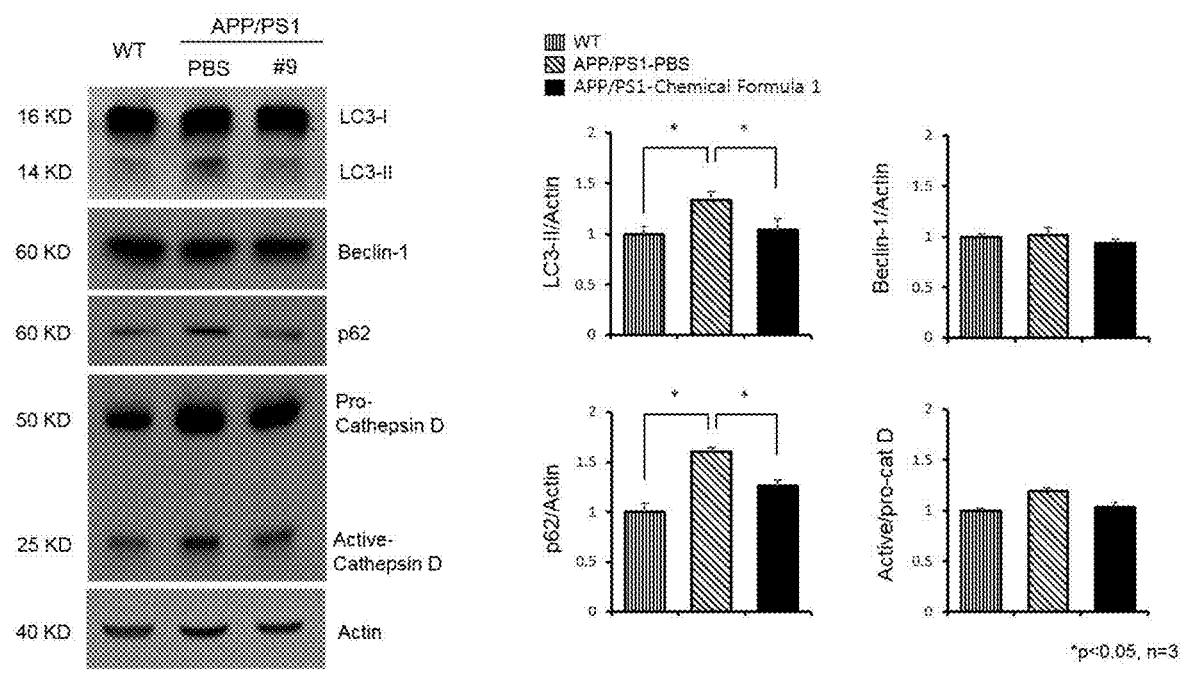
FIG. 7 illustrates a result of graphing the expression of an autophagy-related protein which is analyzed using Western blotting and quantified in the brain cortices of a wild type mouse (WT), an APP/PS1 mouse injected with PBS, and an APP/PS1 mouse injected with an autophagy enhancing compound (n=3/group).

The autophagy occurs through a fusion process of autophagosomes and lysosomes. In the previous study (Korean Patent Registration No. 10-1521117), the present inventors identified that an ideal change in turnover of autophagic vacuoles (AV) is shown in a neurodegenerative disease state such as Alzheimer's disease and abnormal changes occur in which autophagosomes are not degraded but continuously accumulated. As illustrated in FIG. 7, compared to the wild-type (WT) mouse, in the APP/PS1 mouse (untreated), it was confirmed an abnormal change in which the level of LC3-II was increased. On the other hand, it was confirmed that in the APP/PS1 mouse injected with the autophagy enhancing compound, the level of LC3-II was decreased to a level similar to WT, and it is meant that the degradation of autophagic vacuoles was well caused by the compound. It was confirmed that the expression of beclin-1 had no large difference in the three groups.

In addition, the expression of cathepsin D (lysosomal hydrolase) and p62, which are indicators of autophagy turnover, is increased in Alzheimer's patients and pathologically related to Alzheimer's disease. Compared to the WT mouse, it was confirmed that the expression levels of cathepsin D and p62 were increased in the APP/PS1 mouse, and the increased expression levels of cathepsin D and p62 were decreased in the APP/PS1 mouse injected with the autophagy enhancing compound.

Summarizing the above results, it could be seen that the injection of the autophagy enhancing compound in the APP/PS1 mouse reduced Aβ plaque deposition and inflammatory response, and restored damaged autophagy. In addition, it could be seen that the autophagy enhancing compound can be used as a therapeutic agent for degenerative brain disease including Alzheimer's disease by improving learning and memory in an Alzheimer's animal.

INDUSTRIAL AVAILABILITY

As described above, the present invention relates to a novel phenylsulfonyl oxazole derivative and a use thereof and specifically, to a compound represented by Chemical Formula 1 in the present specification or a pharmaceutically acceptable salt thereof, and to a use thereof for prevention, treatment, or improvement of neurodegenerative disease.

The compound of the present invention has a remarkable therapeutic effect, such as reduction of Aβ plaques, alleviation of neuroinflammation, and improvement in memory and anxiety, by regulating abnormal autophagy when applied to neurodegenerative disease such as Alzheimer's disease. Therefore, the compounds of the present application can be very useful for the development of agents for prevention or treatment of neurodegenerative diseases, and thus have great industrial availability.

The invention claimed is:

1. A compound represented by Chemical Formula 1 below or a pharmaceutically acceptable salt thereof:

<Chemical Formula 1>

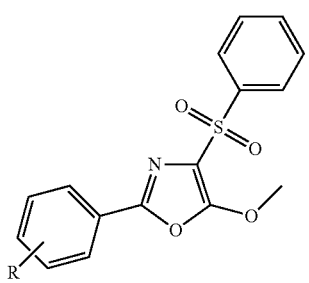

wherein R is selected from the group consisting of halogen-substituted C1-C4 alkyl.

2. The compound or the pharmaceutically acceptable salt thereof of claim 1, wherein the R is trifluoromethyl (—CF$_3$).

3. The compound or the pharmaceutically acceptable salt thereof of claim 1, wherein the compound is 5-methoxy-4-(phenylsulfonyl)-2-(4-(trifluoromethyl)phenyl)oxazole.

4. A composition comprising a compound represented by Chemical Formula 1 below or a pharmaceutically acceptable salt thereof as an active ingredient:

<Chemical Formula 1>

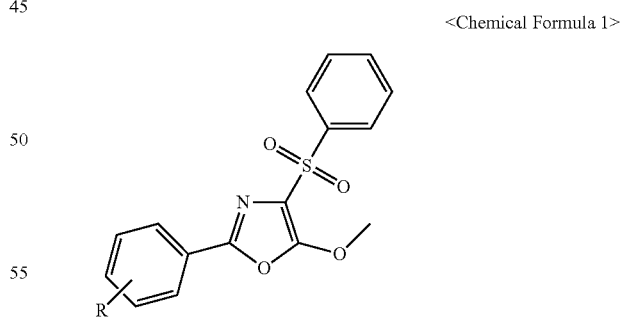

wherein R is selected from the group consisting of halogen-substituted C1-C4 alkyl.

5. The composition of claim 4, wherein the R is trifluoromethyl (—CF$_3$).

6. The composition of claim 4, wherein the composition is a pharmaceutical composition or a food composition.

7. A method for treating neurodegenerative disease in a subject, comprising administering an effective amount of a composition comprising a compound represented by Chemical Formula 1 below or a pharmaceutically acceptable salt thereof as an active ingredient to the subject in need thereof:

<Chemical Formula 1>

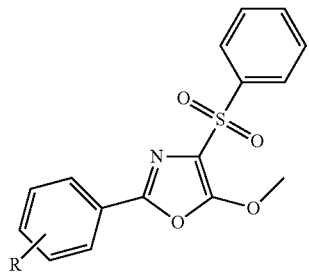

wherein R is selected from the group consisting of halogen substituted C1-C4 alkyl.

8. The method of claim 7, wherein the neurodegenerative disease is at least one selected from the group consisting of Alzheimer's disease, Parkinson's disease, dementia, progressive supranuclear palsy, multi-system atrophy, olive-brain-cerebellar atrophy (OPCA), Shire-Dragger syndrome, striatonigral degeneration, Huntington's disease, amyotrophic lateral sclerosis (ALS), essential tremor, corticobasal degeneration, diffuse Lewy body disease, Parkin's-ALS-dementia complex, pick disease, cerebral ischemia, and cerebral infarction.

9. The method of claim 7, wherein the R is trifluoromethyl (—$CF_3$).

10. The method of claim 7, wherein the compound is 5-methoxy-4-(phenylsulfonyl)-2-(4-(trifluoromethyl)phenyl)oxazole.

* * * * *